(12) United States Patent
Macklin

(10) Patent No.: US 7,347,211 B1
(45) Date of Patent: Mar. 25, 2008

(54) ELECTRICALLY OPERATED SANDER FOR REMOVING CALLUSES AND INCREASING CIRCULATION

(76) Inventor: Elizabeth Macklin, 6331 Sutton Meadows Dr., Houson, TX (US) 77086

( * ) Notice: Subject to any disclaimer, the term of this patent is extended or adjusted under 35 U.S.C. 154(b) by 371 days.

(21) Appl. No.: 11/120,535

(22) Filed: May 3, 2005

(51) Int. Cl.
*A45D 29/05* (2006.01)
*A45D 29/18* (2006.01)

(52) U.S. Cl. .................................. 132/73.6; 132/76.4

(58) Field of Classification Search ............... 132/73.5, 132/73.6, 75.6, 76.4, 76.5; 451/73, 344, 451/340, 360, 361, 356; 601/27–32; 606/133, 606/131; 211/26, 26.2; 248/688, 671
See application file for complete search history.

(56) References Cited

U.S. PATENT DOCUMENTS

| | | | | |
|---|---|---|---|---|
| 2,721,427 A | * | 10/1955 | Dremel | 451/356 |
| 3,938,283 A | * | 2/1976 | Keith, Jr. | 451/344 |
| 3,950,814 A | * | 4/1976 | Fleischhauer | 15/327.7 |
| 4,034,522 A | * | 7/1977 | Miller | 451/340 |
| 4,398,375 A | * | 8/1983 | Malyuk | 451/356 |
| 4,643,207 A | * | 2/1987 | Grahame | 132/73.6 |
| 6,050,270 A | | 4/2000 | Tyshenko, Jr. | 132/73.6 |
| 6,178,970 B1 | | 1/2001 | Purifoy et al. | 132/76.4 |
| 6,523,546 B2 | | 2/2003 | Jo et al. | 132/75.8 |
| 6,551,262 B1 | * | 4/2003 | Lechtman | 601/144 |
| 6,626,746 B2 | * | 9/2003 | Mayr et al. | 451/356 |
| 6,857,948 B2 | * | 2/2005 | Bocka et al. | 451/356 |
| 7,207,875 B2 | * | 4/2007 | Melvin et al. | 451/360 |
| 2006/0272664 A1 | * | 12/2006 | O'Dwyer | 132/73.6 |

* cited by examiner

*Primary Examiner*—Robyn Doan
*Assistant Examiner*—Rachel A. Running
(74) *Attorney, Agent, or Firm*—Goldstein Law Offices P.C.

(57) ABSTRACT

An electrically operated sander for removing calluses and increasing circulation, having a rectangular base unit for insertion into a docking unit. The base unit has a rear end, and includes a movable base plate having rounded edges and a grainy surface area and a gripping handle. The gripping handle extends outwardly from the base unit and defines a curved junction before extending horizontally toward the rear end of the base unit. The base unit houses a motor having a drive shaft mechanically linked to base plate. A rotating two position on-off switch actuates the motor, causing the base plate to vibrate. A rectangular docking unit has a hollow cavity for accepting the gripping handle of the base unit therein for allowing users a hands free method of removing calluses.

2 Claims, 3 Drawing Sheets

ELECTRICALLY OPERATED SANDER FOR REMOVING CALLUSES AND INCREASING CIRCULATION

BACKGROUND OF THE INVENTION

The invention relates to a sander, and more particularly, to a electrically operated sander for removing calluses and dead skin from the soles and undersides of the feet and increasing circulation.

Thick calluses or corns are typically formed on the palms of the hands or the soles of the feet when the epidermis of the palms or the soles becomes partially keratinized due to frequently repeated contact of the hands or feet with a variety of hard or coarse surfaces. Such calluses or corns crack due to, for example, dry or cold weather, thus allowing the dermis under the epidermis to be damaged. Therefore, it is necessary to periodically remove such calluses or corns from the hands or the feet. Such removal of calluses or corns from the hands or feet is commonly called a "pedicure."

U.S. Pat. No. 6,178,970 to Purifoy discloses a portable electric foot sander powered by a rechargeable motor attached to a removable sandpaper or massaging pad for eliminating rough skin and calluses on the feet. U.S. Pat. No. 6,532,546 to Jo discloses a cylindrical pedicure sander comprising a flake brush attached to a shock absorbing unit at each end of the drive shaft. U.S. Pat. No. 6,050,270 to Tyshenko discloses a battery operated, rechargeable fingernail grooming device.

While these units may be suitable for the particular purpose employed, or for general use, they would not be as suitable for the purposes of the present invention as disclosed hereafter.

SUMMARY OF THE INVENTION

It is an object of the invention to produce a means for quickly and efficiently removing calluses from the hands and feet and increasing circulation. Accordingly, the invention is an electrically operated sander for quickly and efficiently removing calluses from the hands and feet and increasing circulation.

It is another object of the invention to provide a means for safely removing calluses and dead and dry skin without cutting or harming the feet or hands of the user. Accordingly, the electrically operated sander of the invention includes a rectangular base unit having a base plate having curved edges and a grainy surface area for safely removing calluses and dead and dry skin without cutting or harming the feet or hands of the user.

It is another object of the invention to provide a simple means for holding the invention while removing calluses. Accordingly, the rectangular base unit includes a gripping handle extending outwardly therefrom for allowing a user to easily hold the electrically operated sander of the invention while removing calluses.

It is another object of the invention to provide a convenient means for allowing hands free use of the invention, as well as storage. Accordingly, the invention includes a substantially rectangular docking unit having a hollow cavity, for accepting the gripping handle of the base unit, such that the grainy surface area is facing upward, thereby allowing the invention to be utilized hands free and easily stored.

It is another object of the invention to provide an effortless means of removing the dead skin. Accordingly, the invention includes a motor within the base unit in communication with an on-off switch for providing power to the base unit for continuously driving the grainy surface area of the base plate in a vibrating manner for effortlessly removing dead skin.

This invention is an electrically operated sander for removing calluses and increasing circulation, having a rectangular base unit for insertion into a docking unit. The base unit has a rear end, and includes a movable base plate having rounded edges and a grainy surface area and a gripping handle. The gripping handle extends outwardly from the base unit and defines a curved junction before extending horizontally toward the rear end of the base unit. The base unit houses a motor having a drive shaft mechanically linked to base plate. A rotating two position on-off switch actuates the motor and causing the base plate to vibrate. A rectangular docking unit has a hollow cavity for accepting the gripping handle of the base unit therein for allowing users a hands free method of removing calluses.

To the accomplishment of the above and related objects the invention may be embodied in the form illustrated in the accompanying drawings. Attention is called to the fact, however, that the drawings are illustrative only. Variations are contemplated as being part of the invention, limited only by the scope of the claims.

BRIEF DESCRIPTION OF THE DRAWINGS

In the drawings, like elements are depicted by like reference numerals. The drawings are briefly described as follows.

DETAILED DESCRIPTION OF THE PREFERRED EMBODIMENTS

Figure 1:
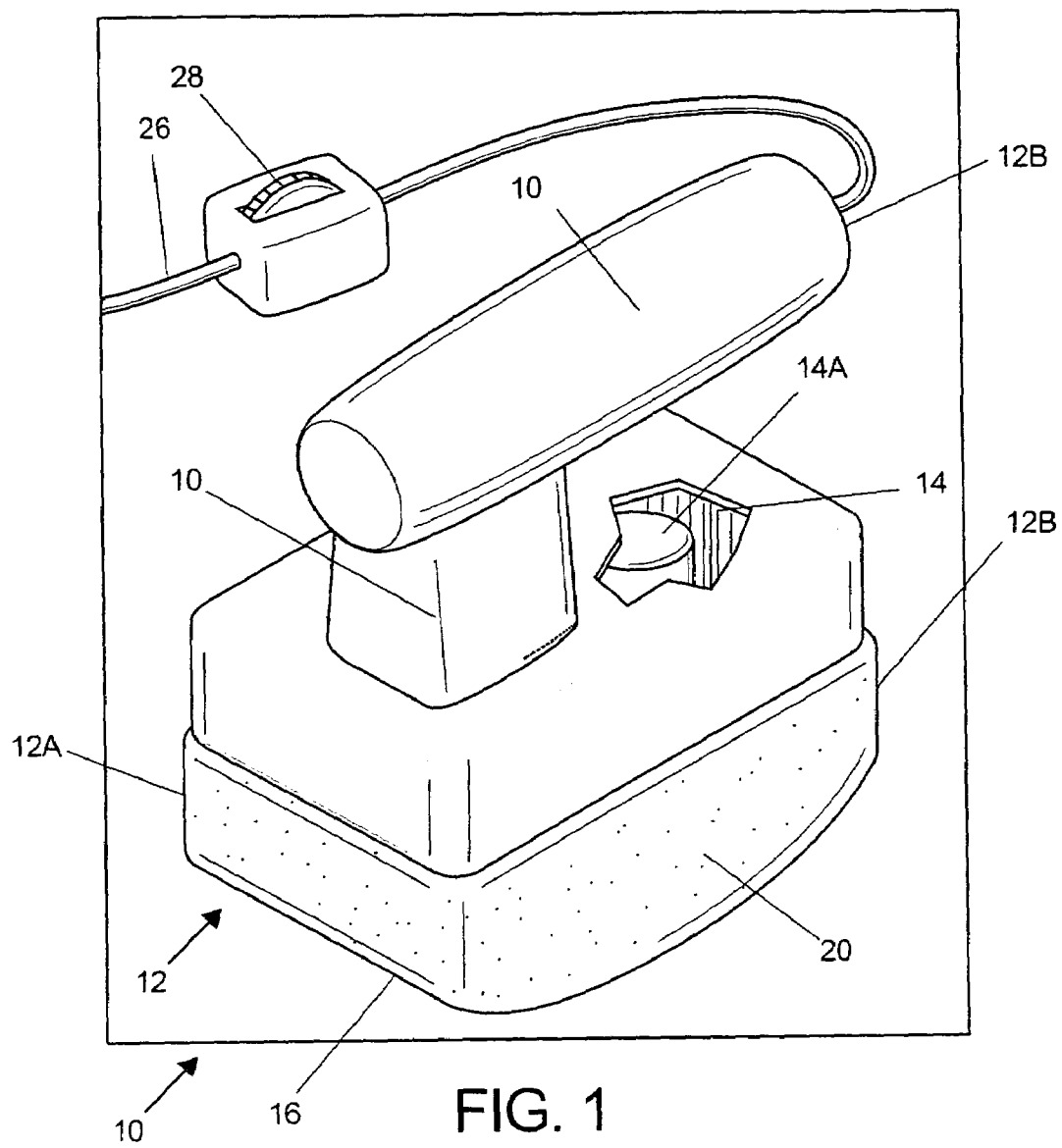
FIG. 1 is a diagrammatic perspective view of an electrically operated sander of the present invention having a rectangular base unit and gripping handle.

FIG. 1 illustrates an electrically operated sander 10 of the present invention for removing calluses and increasing circulation, especially for those with poor circulation and diabetes. The electrically operated sander 10 includes a substantially rectangular base unit 12 housing a motor 14. Preferably, the motor 14 is rated at 0.8 amperes, 120 volts, and rotates at a speed of 12,000 rpm. The motor 14 includes a drive shaft 14A.

The base unit 12 includes a movable base plate 16 having rounded edges 18 and a grainy surface area 20. The base unit 12 is mechanically linked to the drive shaft 14A of the motor 14. Such that when power is applied through the base unit 12, the motor 14 continuously drives the base plate 16 and allows the graining surface area 20 to vibrate thereby conveniently, safely and easily removing dead skin and calluses from hands and feet of the user.

The base unit 12, preferably sturdy plastic, has a forward end 12A and a rear end 12B. A gripping handle 22 extends outwardly from the forward end 12A, defines a curved junction 24, and extends horizontally toward the rear end 12B for allowing the user to hold the base unit 12 during callus removal. The gripping handle 22 includes a rear end 22A. A power cable 26 extends outwardly from the rear end 22A of the gripping handle 22 and is inserted into a standard electrical outlet for powering the motor 14. The power cable 26 includes a rotating two position on-off switch 28, having both an on position and an off position, for actuating the motor 14 and causing the base plate 16 to vibrate.

Figure 2:
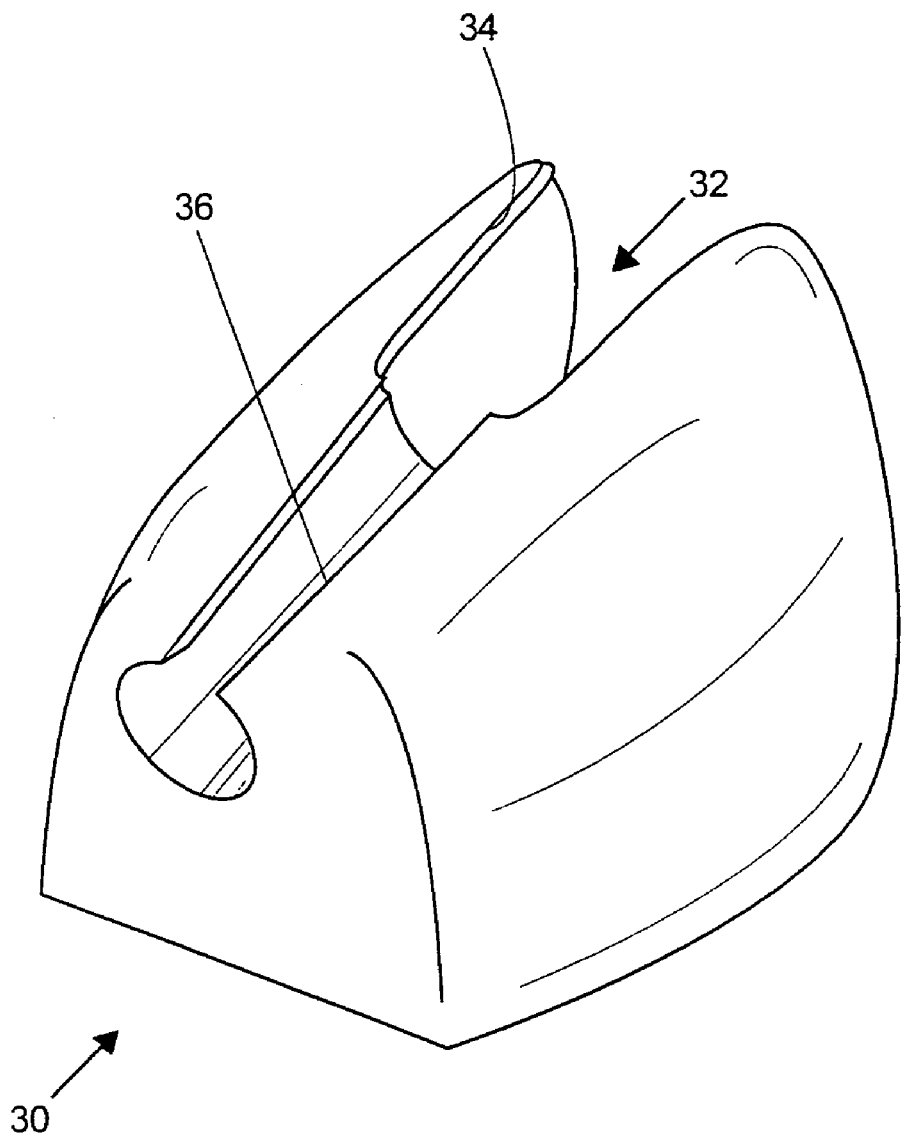
FIG. 2 is a diagrammatic perspective view of a rectangular docking unit of the electrically operated sander of the present invention, having a hollow cavity.

FIG. 2 illustrates the electrically operated sander 10 of the present invention having a substantially rectangular docking unit 30. The docking unit 30 includes a hollow cavity 32 for accepting the gripping handle 22 of the base unit 12 therein, shown in FIG. 3. The docking unit 30 holds the base unit 12 and can provide users with a hands free method of removing calluses by simple positioning hands and feet directly onto the grainy surface area 20 while in the docking unit 30 and turning the on-off switch 28 to on, which starts vibrating the base plate 16, shown in FIG. 3. In addition, the docking unit 30 has tapered opening 34 and an elongated slit 36.

Figure 3:
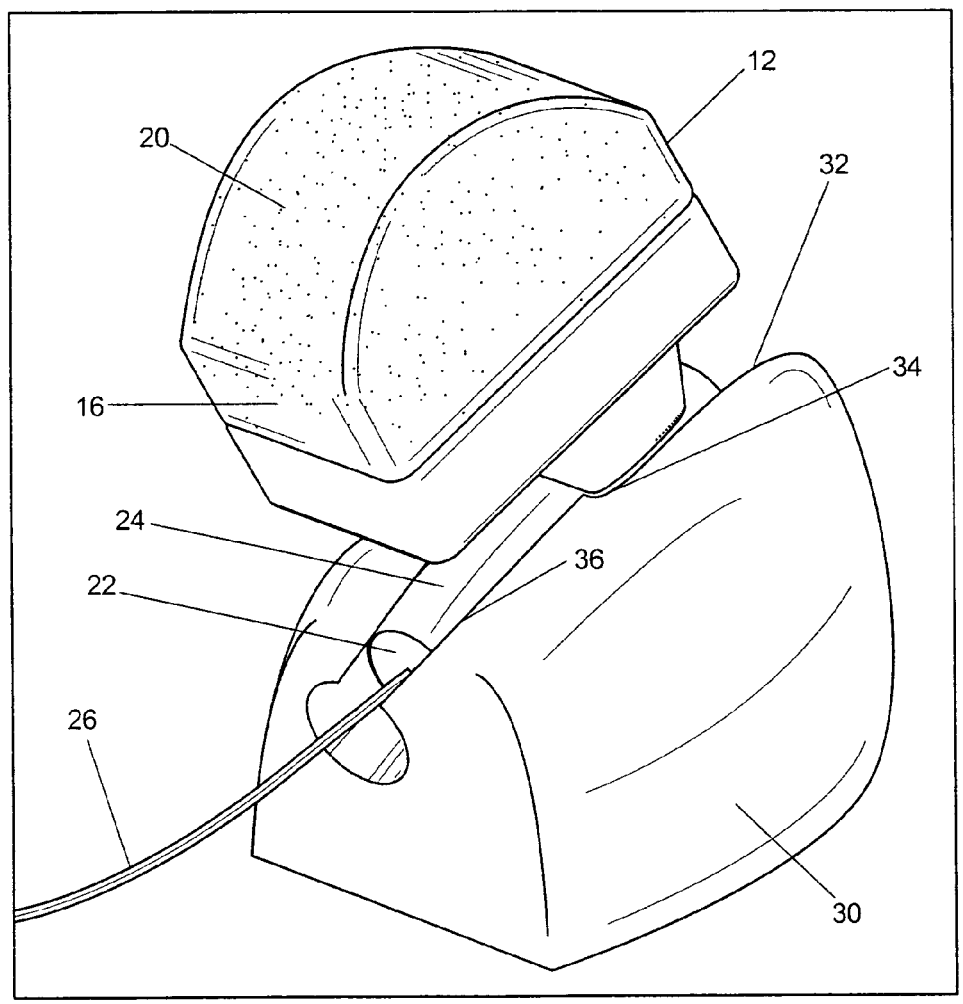
FIG. 3 is a diagrammatic perspective view of the electrically operated sander of the present invention allowing hands free use while the base unit is resting in the docking unit.

FIG. 3 illustrates the base unit 12 securely resting within docking unit 30 and positionable for hands free use. The tapered opening 34 allows the curved junction 24 of the gripping handle 22 of the base unit 12 to rest stationary and securely within the hollow cavity 32 without moving from side-to-side. Here, the when the base unit 12 is inserted into the docking unit 30 the power cable 26 fits through the elongated slit 36 and can extend outwardly from the hollow cavity 32 without being tampered with or harmed.

In use, a user simply positions the base unit 12 into the docking unit 30 as shown, and inserts the power cable 26 into an electrical outlet. Next, the user actuates the on-off switch to the on position, causing the motor to continuously drive the base plate 16 in a vibrating motion. Then the user simply positions his/her calluses, on either his/her hands or feet, against the grainy surface area 20 of the base plate 16 and applies slight pressure while the dry and dead skin is slowly removed and shed from the hand or foot. After use, the user simply removes his/her hand or foot, and actuates the on-off switch to the off position.

In additional embodiments, the invention may be wireless and receive power from rechargeable batteries. Here, the rechargeable batteries are housed within the base unit 12, while the on-off switch 28 is coupled to the gripping handle 22.

In conclusion, herein is presented an electrically operated sander for removing calluses. The invention is illustrated by example in the drawing figures, and throughout the written description. It should be understood that numerous variations are possible, while adhering to the inventive concept. Such variations are contemplated as being a part of the present invention.

What is claimed is:

1. A hands free method of removing calluses from hands or feet using an electrically operated sander, having a base unit having an on-off switch having an on position and an off position, a motor, a base plate having a grainy surface area, and having a docking unit, the steps comprising:

positioning the base unit into the docking unit;

vibrating the grainy surface of the base plate by actuating the on-off switch to the on position; and positioning calluses against the grainy surface and applying slight pressure while calluses are slowly removed.

2. The hands free method of removing calluses from hands or feet using an electrically operated sander of claim 1, the steps further comprise removing hands or feet from the grainy surface area and turning the on-off switch to the off position.

* * * * *